United States Patent [19]

Ng

[11] Patent Number: 5,128,216
[45] Date of Patent: Jul. 7, 1992

[54] LUBRICANTS FOR MAGNETIC MEDIA
[75] Inventor: Quock Ng, Colorado Springs, Colo.
[73] Assignee: Digital Equipment Corporation, Maynard, Mass.
[21] Appl. No.: 543,698
[22] Filed: Jun. 26, 1990
[51] Int. Cl.$^5$ .............................................. G11B 5/00
[52] U.S. Cl. .................... 428/695; 428/694; 428/900; 428/64; 252/62.54; 252/58; 558/80
[58] Field of Search ............. 428/694, 695, 900, 338; 558/80; 564/13; 252/62.54, 58

[56] References Cited

U.S. PATENT DOCUMENTS

| | | | |
|---|---|---|---|
| Re. 33,273 | 7/1990 | Speaker | 210/639 |
| 3,316,330 | 4/1967 | Nichols | 558/80 |
| 4,554,076 | 11/1985 | Speaker | 210/639 |
| 4,613,548 | 9/1986 | Lum | 428/411.1 |
| 4,668,587 | 5/1987 | Sumiya et al. | 428/411.1 |
| 4,844,991 | 7/1989 | Miura et al. | 428/694 |
| 4,871,625 | 10/1989 | Dekura et al. | 428/695 |

OTHER PUBLICATIONS

Rätz, Rudi A new class of stable phosphonitrilic acid esters polyfluoroalkyl phosphnitrilates JACS 84 (1962) pp. 551–555.
Hoshino, et al., "Lubrication Layer Using Perfluoropolyether and Aminosilane for Magnetic Recording Media," undated typed paper.
U.S. Serial No. 07/369,713, Jun. 22, 1989, Schmidt.
"Novel Lubricants For Magnetic Thin Film Media", PMRC '89 Proceedings, Aug. 29–31, 1989.
"Characterization of Monolayer and Bilayer (Polymer Monolayer) Structures For Their Use As a Lubricant", Thin Solid Films, 160 (1988) pp. 453–462.
"Langmuir-Blodgett Films", Physics Today, Jun., 1988.

*Primary Examiner*—Merrell C. Cashion, Jr.
*Assistant Examiner*—Stevan A. Resan
*Attorney, Agent, or Firm*—Arnold, White & Durkee

[57] ABSTRACT

Amphiphilic compound having one of the following structures:

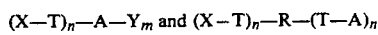

$$(X-T)_n-A-Y_m \text{ and } (X-T)_n-R-(T-A)_n$$

wherein X is a fluorocarbon terminal group, T is a polar linking group, A is a nucleus other than saturated lower aliphatic, Y is a polar nonlinking group, R is a saturated or unsaturated, substituted or unsubstituted, straight or branched lower aliphatic group, n is at least one, and the sum of n and m is at least two. Such compounds are useful as lubricants for magnetic media. Also, a lubricated magnetic medium comprising a planar, polar surface covered with a monolayer comprising a compound having the structure described above, except that A can also be a saturated lower aliphatic group.

2 Claims, 1 Drawing Sheet

LUBRICANTS FOR MAGNETIC MEDIA

FIELD OF THE INVENTION

The present invention relates generally to novel amphiphilic compounds. (Amphiphilic compounds are defined as compounds having at least one polar portion and at least one nonpolar portion, which are capable of forming Langmuir-Blodgett films.) The present invention relates more particularly to amphiphilic compounds in which each nonpolar portion is a fluorocarbon and each polar portion is capable of bonding to a polar surface. These compounds have utility as lubricants to protect metal, metal oxide, carbon, or other surfaces of thin film magnetic recording media useful in data, audio, and video recording from wear and corrosion. The present invention also relates to a novel thin-film magnetic medium comprising a polar surface of the magnetic medium, coated by and bonded to a monolayer of at least one of the present amphiphilic compounds.

BACKGROUND OF THE INVENTION

Magnetic media are used in the form of tapes, floppy disks, hard disks, and the like to store magnetic impulses received from a recording or write head scanned on the medium and to reconstruct the same impulses in a playback or read head scanned on the same part of the medium. The write and read functions of a computer disk system are commonly performed by a single read/write head. The head moves rapidly with respect to the magnetic medium and closely approaches it, momentarily coming into direct contact with it when the head starts or stops scanning. The industry has found it necessary to lubricate the magnetic medium so friction between the medium and head does not rapidly destroy the head or the medium.

Computer data storage media such as oxide disks have been coated with a 30 to 120 Angstrom layer of fluorinated oil to reduce friction while the head is in contact with the disk, and to protect the disk from corrosive atmospheric contaminants. This coating has worked well for systems achieving densities of no more than about 60 to 100 megabytes per square inch, wherein the read/write heads fly relatively high over the recording medium, riding on an air cushion. Other materials which have found utility as lubricants for magnetic media used with high-flying read-write heads include fluorinated oils (particularly perfluoropolyethers), fatty acids and their esters, organosilanes, and organoaminosilanes.

In higher-density magnetic storage systems currently under development, the read/write heads will fly lower. The lubricant layer for such heads will typically be much thinner—perhaps less than 30 Angstroms thick. Such a thin layer of a conventional lubricant will not lubricate the magnetic medium sufficiently to allow it to withstand the increased friction resulting from repeated scanning by low-flying heads.

Another problem in the art is degradation of the lubricant. Fatty aliphatic chains (broadly defined herein as those having from 6 to 22 carbon atoms) degrade with each read/write cycle, forming a buildup of sludge. This sludge causes higher friction between the magnetic medium and the head, head instability, and increased spacing between the head and the medium surface. Deterioration of performance is the practical result.

Thus, a need has arisen for new lubricants which will durably adhere to the disk in thin layers, will allow repeated read/write cycles without an increase in friction or sludge buildup, will offer corrosion protection, and will provide better lubrication in the environment of a low flying read/write head.

SUMMARY OF THE INVENTION

One aspect of the invention is an amphiphilic compound having one of the following structures:

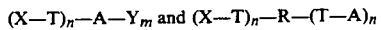

wherein X is a fluorocarbon terminal group, T is a polar linking group, A is a nucleus other than saturated lower aliphatic, Y is a polar nonlinking group, R is a straight or branched, saturated or unsaturated, substituted or unsubstituted lower aliphatic group, n is at least one, and the sum of n and m is at least two. Such compounds are improved lubricants for magnetic media.

Another aspect of the invention is a lubricated magnetic medium comprising a planar, polar surface covered with a monolayer comprising a compound having the structure described in the preceding paragraph, except that A includes saturated lower aliphatic groups in this embodiment of the invention. The present lubricants bond more tightly to the substrate, are less easily degradable, and provide better lubrication and corrosion protection than the lubricants of the prior art.

DETAILED DESCRIPTION OF THE INVENTION

Figure 1:
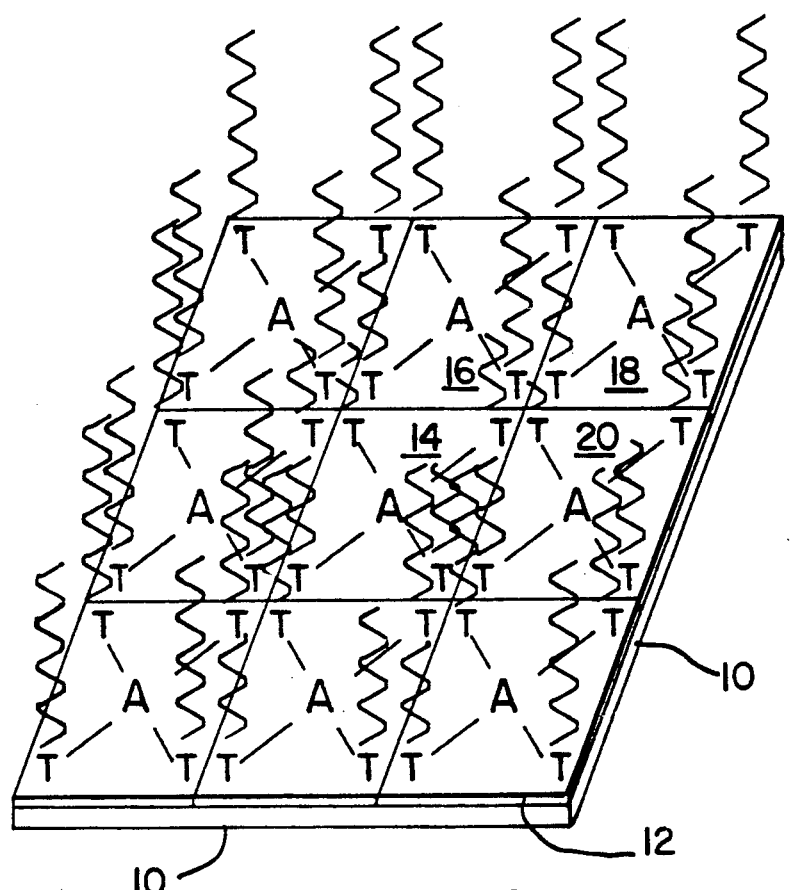
FIG. 1 is a diagrammatic perspective view of the surface of a magnetic medium, coated with a lubricant according to the present invention.

While the invention will be described in connection with certain preferred embodiments, it will be understood that the invention is not limited to the preferred embodiments. On the contrary, the invention includes all alternatives, modifications, and equivalents as may be included within the spirit and scope of the invention as defined by the appended claims. In the present disclosure, it is assumed that where more than one substituent of a particular kind is to be selected, each selection is made independently, so the several substituents of the same kind may be the same or different.

The present compounds are amphiphilic compounds having a general structure selected from the group consisting of:

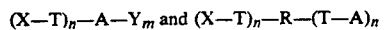

X in each structure is broadly defined as a fluorocarbon. Exemplary fluorocarbons are selected from the group consisting of:

i. branched or (preferably) straight-chain perfluoroalkyl moieties having from about 6 to about 22, preferably 6-12 carbon atoms. Several examples of this type are perfluoro-n-octyl ($C_8F_{17}$—), perfluoro-n-decyl ($C_{10}H_{21}$—), and perfluoro-n-dodecyl ($C_{12}H_{25}$—) moieties.

ii. perfluoroalkyl-terminated lower aliphatic moieties including a perfluoroalkyl terminal group as described above and a straight or branched chain, saturated or unsaturated, unsubstituted or substituted lower aliphatic linking group having from 1 to about 5 aliphatic carbon atoms. The permissible substituents to the lower aliphatic linking group include lower aliphatic, cycloaliphatic, and aryl moieties as defined elsewhere herein and one or more heteroatomic substituents selected from nitrogen, phosphorus, sulfur, oxygen, halogen, silicon, and combinations thereof. Exemplary heteroatomic substituents contemplated herein are the following:

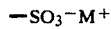

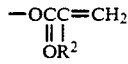

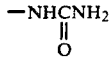

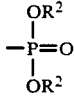

—OSO$_3$—

Specific examples of perfluoroalkyl-terminated lower aliphatic moieties useful herein include perfluoro-n-dodecylmethylene and perfluoro-n-octyl-t-butylene.

iii. lower aliphatic-linked perfluoropolyethers having from about 6 to about 22 carbon atoms. The perfluoropolyethers contemplated herein are straight- or branched-chain perfluoroalkylene moieties having from 1 to about 5 carbon atoms, linked to form chains having a total of from about 6 to about 22 carbon atoms by ether linkages (—O—). The aliphatic linking groups are lower aliphatic moieties as defined above. An exemplary perfluoropolyether moiety useful herein is the following:

HOCH$_2$CF$_2$O(CF$_2$O)$_a$(CF$_2$CF$_2$O)$_b$CF$_2$CH$_2$ wherein b is a number between 3 and 100, a is an integer greater than or equal to zero, a+b is no greater than 100, optionally no greater than 50, and the perfluoromethylene and perfluoroethylene moieties are randomly distributed in the chain.

iv. perfluoroalkyl moieties as previously defined, having one fluorine atom of the terminal trifluoromethyl moiety replaced by hydrogen. An exemplary substituted perfluoroalkyl group is 11H-eicosafluorodecyl:

H—(—CF$_2$—)$_{10}$—

Going back to the general structures of the present lubricants, A is a nucleus. A is selected from the group consisting of:

i. substituted or unsubstituted, straight or branched, unsaturated lower aliphatic moieties as previously defined (except excluding saturated aliphatic moieties).

An example of this category of nuclei is 2-butenyl:

—CH$_2$—CH=CH—CH$_2$— ii. saturated and unsaturated cycloaliphatic having from about 4 to about 8 ring carbon atoms. Examples of this category of nuclei include cyclobutane and cyclohexene.

iii cycloaliphatic substituted by at least one moiety selected from the group consisting of heteroatoms as previously defined (as ring or non-ring substituents) and lower aliphatic as previously defined (including saturated lower aliphatic moieties). Exemplary moieties include those having the following structures:

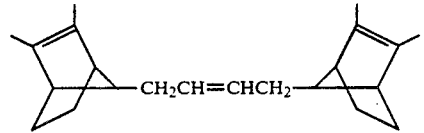

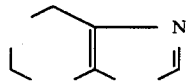

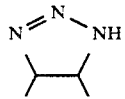

and tetramethyltetrapropylenecyclotetrasiloxane.

iv. arylene having from 1 to about 30 carbon atoms, including monocyclic and polycyclic rings, for example:

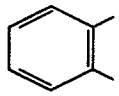

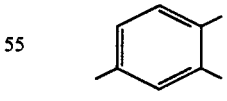

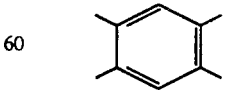

and naphthalene;

v. arylene substituted by at least one moiety selected from the group consisting of lower aliphatic, cycloaliphatic, and heteroatoms, all as most broadly defined previously. The following are examples:

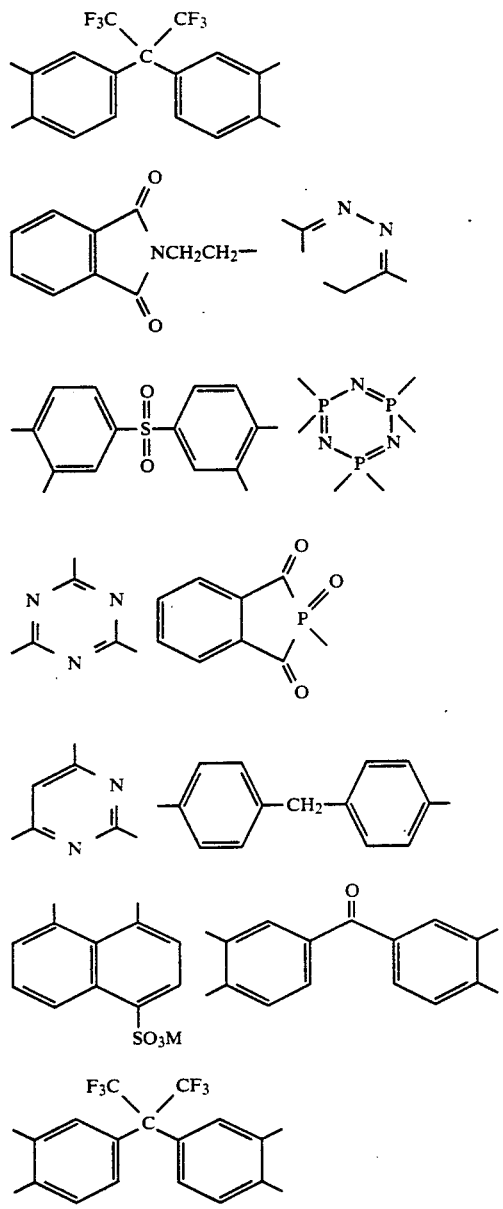

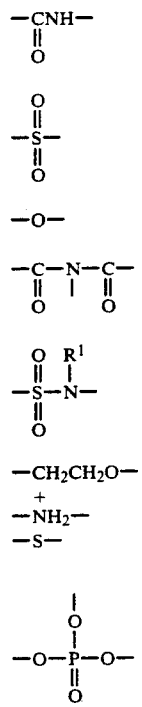

In the preceding formulas, M is a cation, for example, an alkali or alkaline earth metal. Specific metals contemplated as cations herein are potassium, sodium, and magnesium. Further examples of nuclei usable herein are those of porphyrin and cyclic sulfides.

In the formula of the present compounds first set out above, each T represents at least one polar linking moiety. The purposes of the linking moieties are to provide strong orientation affinity to the aqueous phase during LB film deposition (as described below) and subsequently to anchor the lubricant to a substrate.

Exemplary T moieties are selected from the group consisting of:

—CO—
 ‖
 O

—NH—

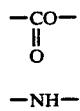

—CNH—
 ‖
 O

O
‖
—S—
‖
O

—O—

—C—N—C—
 ‖  |  ‖
 O     O

O  R$^1$
 ‖  |
—S—N—
 ‖
 O

—CH$_2$CH$_2$O—

—$\overset{+}{\text{NH}_2}$—

—S—

$\underset{\underset{\text{O}}{\|}}{\overset{\overset{\text{O}}{|}}{-\text{O}-\text{P}-\text{O}-}}$ $-\overset{+}{\underset{|}{\text{NH}}}-$

—N—
 |

—C—
 ‖
 O

Where present in the foregoing formulas, R$^1$ is selected from hydrogen and lower aliphatic, as most broadly defined above to include saturated as well as unsaturated moieties. Though not shown, an anion, for example halide or hydroxide, is associated with each quaternary nitrogen atom in the foregoing formulas. Linkages comprising chains of more than one of the polar linking moieties illustrated herein are also contemplated.

Each Y of the general structures of the present compounds comprises a polar nonlinking moiety. (Nonlinking moieties are defined herein as those which do not directly or indirectly link a fluorocarbon moiety to a nucleus.) If more than one T group is present in the molecule, Y is an optional substituent herein. Y is preferably selected from the group consisting of:

—SO$_3^-$M$^+$

—CZ
 ‖
 O

=S
=O

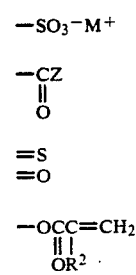

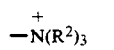

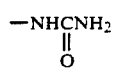

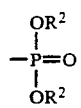

In the foregoing formulas, M is a cation as previously defined, Z is halide, and R² is selected from hydrogen and lower aliphatic as previously defined.

R in the foregoing general structures is selected from saturated and unsaturated, substituted and unsubstituted, straight and branched lower aliphatic linkages having from 1 to about 5 carbon atoms. Examples of R linkages are:

—CH₂CH₂— (ethylene); and

C(—CH₂—)₄ (neopentylene).

In the general formulas first given above, n is at least one and the sum of n and m is at least two. Thus, each molecule has at least one polar linking moiety and a second polar moiety (which can be linking or nonlinking). There is no critical upper limit to the values of m, n, or their sum. Values of up to 18 (see Example 3 below) are illustrated herein for the sum of m plus n.

Compounds as described herein may be made using any of a variety of synthetic methods. A preferred method contemplated herein, and illustrated in the examples, is to react 1) a fluorocarbon having a terminal functional group with 2) a precursor of the nucleus having one or (preferably) more functional groups. The reaction of the functional groups of the fluorocarbon and the precursor provides a polar linkage joining the two to form a compound according to the present invention. Thus, an X-T-A, X-T-R, or R-T-A moiety defined according to the general formulas herein can be created by carrying out a single reaction.

For example, bis-nadic-anhydrybutene is a nucleus precursor having the following structure:

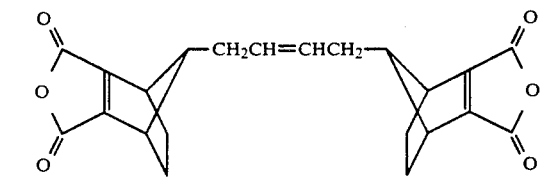

In the foregoing structure, the functional groups are two cyclic anhydride groups. One equivalent of bis-nadicanhydrybutene can be reacted with four equivalents of a hydroxy-terminated fluorocarbon, such as a fluoroalcohol having the following structure:

C₁₂F₂₅CH₂CH₂OH to form a compound according to the present invention having the following structure:

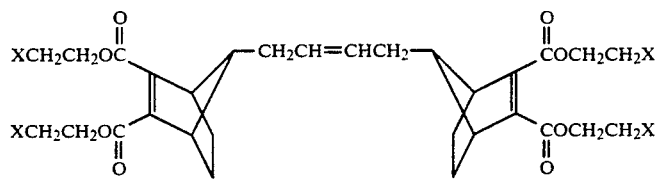

in which each X of the general formulas represents a C₁₂F₂₅— terminal group, each T is an ester linkage, n is 4, A is:

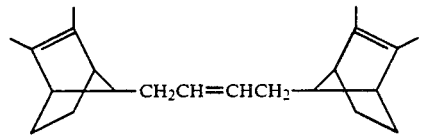

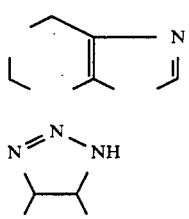

and m is zero, so there is no Y present.

Thus, one class of the present compounds can be prepared by reacting an anhydride or a corresponding free carboxylic acid, for example, any of the following:
4,4'-(hexafluoroisopropylidene)diphthalic anhydride;
3,3'4,4'-benzophenone tetracarboxylic dianhydride;
pyromellitic dianhydride;
1,2,3,4-cyclobutane tetracarboxylic dianhydride;
4-sulfo-1,8-naphthalic anhydride potassium salt;
2-sulfobenzoic acid cyclic anhydride;
trimellitic anhydride chloride;
4,5-dicarboxy-1,2,3-triazole; and
bis-nadic-anhydrybutene with any of the following hydroxy-terminated fluorocarbons:
[C₈F₁₇SO₂N(C₂H₅)CH₂CH₂O]₂—P(O)OH;
perfluoroalkyl hydroxyalkyl sulfamides, for example:
C₈F₁₇SO₂NH(CH₂CH₂OH);
HOCH₂CF₂O(CF₂O)ₙ(CF₂CF₂O)ₘCF₂CH₂OH;

$C_8F_{17}CH_2CH_2OH$; and
$C_{12}F_{25}CH_2CH_2OH$
in an ordinary esterification reaction. Acid, anhydride, or other nucleus precursors can also react with a hydroxy-terminated fluorocarbon, such as tri(2-perfluoro-n-octyl)-ethyl citrate (TPFC):

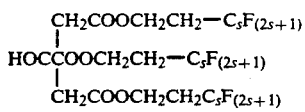

in which s is 8 to form the present compounds. The triperfluoro-n-octyl citrate starting material illustrated above is not within the definition of the present novel compounds, but is contemplated to be useful per se as a lubricant herein.

Another type of the present compounds can be prepared by reacting an imide or an amine functional group of a nucleus precursor with a carboxylic acid, alcohol, non-fluorine halide (i.e., chloride, bromide, or iodide), or non-fluorine acid halide functional group of a fluorocarbon. Exemplary imides are as follows:
pyromellitic diimide;
N-(2-hydroxyethylphthalimide;
4,5-dichlorophthalimide; and
N-2-bromoethylphthalimide.

Exemplary amines and related materials are:
bis(3,4-diaminophenyl)sulfone; melamine;
2,4,6-triaminopyrimidine;
6-thioanthine; and
3,5-diamino-1,2,4-triazine.

Exemplary halogen, acid halide, and carboxylic acid functional fluorocarbons for the above reaction are:
perfluorododecyl iodide, $CF_3(CF_2)_{11}I$;
perfluoro-1-octanesulfonyl fluoride,
$CF_3(CF_2)_7SO_2F$;
11H-Eicosafluorodecanoyl chloride, $H(CF_2)_{10}COCl$;
$C_8F_{17}CH_2CH_2I$;
$C_{10}F_{21}CH_2CH_2I$;
$C_{12}F_{25}CH_2CH_2I$;
perfluorodecanoic acid (PFDA), $C_9F_{19}COOH$;
$(C_{10}F_{21}CH_2CH_2S)_2C(CH_3)CH_2CH_2CO_2H$; and
$F[CF(CF_3)CF_2O]_nCF(CF_3)CO_2H$, n=2-50.

In addition, the fluoroalcohols previously listed, such as triperfluoro-n-octyl citrate, can also be converted to tosylates, which can then be reacted with the foregoing amines and imides.

An example of the reaction products and novel lubricants derivable from the exemplary amines, imides and fluorocarbons is the perfluorododecyl iodide salt of bis(3,4-diaminophenyl)sulfone:

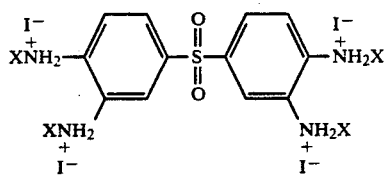

wherein each X is a perfluoro-n-dodecyl moiety.

Another class of compounds according to the present invention is the reaction product of a chloride precursor of a nucleus with a fluorocarbon having a carboxylic acid or hydroxy functional group. For example, any of the following chlorides:
phosphonitrilic chloride trimer (PNC);
cyanuric chloride (CCl); or
1,2-phenylene phosphorochloride;
can be reacted with any of the carboxylic acid or hydroxy functional fluorocarbons described above. For example, PNC can be reacted with TPFC or CCl can be reacted with PFDA.

The chlorides previously described can also be reacted with perfluorosulfonyl alkyl amides as previously described (which are the reaction products of fluorocarboxylic acids and alkylsulfonamides). For example, the reaction product of phosphonitrilic chloride trimer with perfluoro-n-octyl-2-hydroxyethylsulfonamide has the following structure:

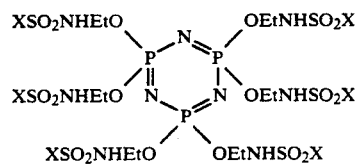

wherein X is a perfluoro-n-octyl moiety.

Another class of useful nucleus precursors is a diisocyanate or a polyisocyanate terminated precursor, which can react with a carboxylic acid, hydroxy, or amine functional group of a fluorocarbon to yield an carbamate linkage. An exemplary diisocyanate nucleus precursor contemplated herein is diphenylmethane-4,4'-diisocyanate.

Acrylates are another class of nucleus precursors useful herein,. Exemplary acrylates have the following structures:
2-hydroxyethyl acrylate, $CH_2{=}CHCOOCH_2CH_2OH$;
pentaerythritol triacrylate (PETA),
$(CH_2{=}CHCOOCH_2)_3CCH_2OH$;
2-isocyanatoethyl methacrylate,
$CH_2{=}C(CH_3)COOCH_2CH_2NCO$; and
glycidyl methacrylate, $CH_2{=}C(CH_3)$

An example of the novel lubricants derivable from the reaction of acrylates and fluorocarbons is an ester of $[C_8F_{17}SO_2N(C_2H_5)CH_2CH_2O]_2$—P(O)OH and PETA. The resulting product has the following formula:

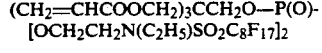

This lubricant can be further cross-linked through its three acrylates to form a mechanically strong film. The structure immediately above fits into the general structural formula:

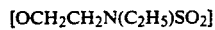

as follows. X is perfluoro-n-octyl; the n associated with X is two; the T associated with X is:

$[OCH_2CH_2N(C_2H_5)SO_2]$ (which is a chain of three polar groups as previously identified); the n associated with X is two, R is:

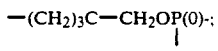

each of the T's associated with each A is an ester linkage, A is CH$_2$=CH—, and the n associated with A is 3. This formula thus illustrates that each T can be a string of polar groups as individually identified previously, within the scope of the present invention.

LUBRICATED MAGNETIC MEDIUM

Another aspect of the invention is a lubricated magnetic medium comprising a planar, polar surface of the medium covered with a monolayer comprising a compound having the structure described in the preceding description, except that A can also be a saturated lower aliphatic group in this embodiment of the invention.

The monolayer may be a Langmuir-Blodgett (LB) monolayer less than 120, preferably less than 70, most preferably less than 30 Angstroms thick. The monolayer may also be applied to the substrate in another manner. A background on the nature and formation of LB films and the amphiphilic materials capable of forming LB films is provided in Agarwal, "Langmuir-Blodgett Films," *Physics Today*, Jun., 1988. "Amphiphilic" is also defined in this reference. The definition of "amphiphilic" and the description of LB films in the Agarwal reference are hereby incorporated herein by reference.

Generally speaking, an LB film is a tightly packed single layer of amphiphilic molecules oriented with their hydrophilic ends (here, the two or more T and Y moieties) adjacent to the substrate and their hydrophobic ends (here, the X moieties) standing above the substrate.

While the novelty or scope of the invention does not depend on the accuracy of this theory, it is contemplated that the compounds of the present invention provide superior, durable lubrication because the T and Y moieties of the present compounds, as well as any polar moieties included in the structure of A and R, are bonded securely to the polar surface of the magnetic medium by Van der Waals forces between the free electron pairs of the polar moieties and oxygen atoms present in the magnetic medium. (A typical thin-film magnetic medium has either a metal oxide surface or a carbon surface which oxidizes due to its exposure to air.) Dipole interactions and ionic or electrostatic attraction also contribute to bonding.

For the preferred compounds in which A is a planar and aromatic heterocyclic ring, the ring will interact with the pi-electrons of an amorphous carbon magnetic recording disk protective coating. Additionally, the amine salts will interact with and form strong bonds with a spontaneously oxidized carbon surface.

Because of these bonds between each lubricant molecule and the substrate, the A and R moieties associated with the polar groups are closely packed (due to Van der Waals attractive forces between the polar moieties of adjacent molecules), and are fixed substantially in a lubricant plane parallel to the polar surface of the magnetic medium. The X moieties, which are very nonpolar, extend substantially perpendicularly above the lubricant plane, which is how they are oriented when an LB film of the lubricant is applied to the magnetic medium. Since each fluorocarbon moiety is linked to the nucleus by a polar linking group, the base of each fluorocarbon chain is anchored to the substrate.

The several fluorocarbon moieties of a lubricant are preferably identical, are each anchored at one end in identical fashion, and extend perpendicularly upward from the substrate. The fluorocarbon chains are zig-zag chains, as dictated by their tetrahedral bond geometry. This symmetrical arrangement means that the corresponding atoms of each fluorocarbon chain are disposed the same distance above the substrate, so the fluorocarbon chains have a tendency to nest, allowing close packing of the chains.

The nuclei of the monolayer are tightly packed and the X moieties are numerous and preferably identical, so the X moieties stand like blades of grass above the substrate, providing a dense, durable lubricating layer which interfaces with a scanning read/write head to reduce friction.

Figure 2:
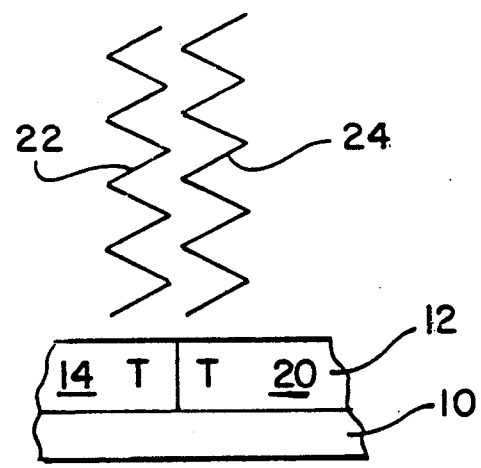
FIG. 2 is a fragmentary side elevational view of the structure shown in FIG. 1.

This theory is illustrated in FIGS. 1 and 2. FIG. 1 schematically shows a section of the substrate 10 covered by an array of closely packed rectangular "tiles" such as 12, each representing the nucleus A and the four polar linking groups T of the following molecule illustrated above:

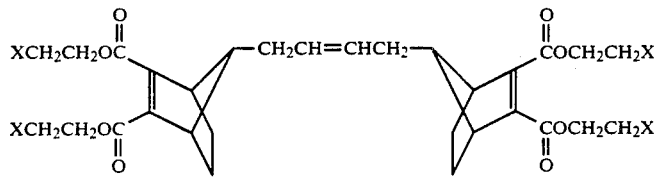

At the intersecting corners such as 14, 16, 18, and 20 of four adjacent molecules, Van der Waals forces cause the T moieties to be mutually attracted, and each T is anchored to the substrate 10 because it tends to rotate around its single bond with the nucleus A until its carbonyl moiety is oriented in a position of maximum attraction to the substrate below (with the carbonyl double bond parallel to the lubricant plane).

Many X fluorocarbon chains—there is one X chain per T linking group—are omitted from FIG. 1 to more clearly illustrate the lubricant plane defined by the molecules such as 12. Since the four T moieties of the intersecting corners such as 14-20 of adjacent molecules are closely packed, the fluorocarbon moieties associated with each linking group are equally closely packed at their bases.

Referring to FIG. 2, two of the four X moieties of a set of intersecting corners (such as 14-20) are shown from the side. The fluorocarbon chains 22 and 24 are identical, and thus are capable of nesting because their respective backbone atoms line up, much like the crystalline structure of an oriented polyolefin film. This arrangement allows many fluorocarbon chains to be disposed perpendicular to the lubricant plane defined by the molecules such as 12.

The lubricants described herein are applied in essentially conventional fashion to thin-film magnetic media, for example, using the LB coating technique. While only one Z-type monolayer of the present lubricants can bond directly to the substrate, more than one Z-type layer (with the fluorocarbon chains extending away from the substrate, as shown in the figures) can be built up by the LB film formation method. This may be done to ensure complete coverage of the substrate by a monolayer, particularly if the substrate surface is uneven. The present lubricant layers can also be overcoated with another lubricant, for example a fluorocarbon oil which is compatible with the fluorocarbon chains of the LB monolayer.

Before applying a LB monolayer of the present lubricants, it is important to thoroughly clean the magnetic medium surface, as by immersion in a solvent such as isopropanol followed by rinses of deionized water, until the surface to be coated has a high electrical resistance (for example, about 18 megohms per square).

EXAMPLES

The following working examples provide further exemplification of the broad scope of the present invention, and enable one of ordinary skill in the art to carry out the present invention.

EXAMPLE 1

Triaminopyrimidine salts of perfluoropolyether acid, with three long chain perfluorocarbons moieties on a nitrogen heterocyclic ring, were prepared as follows:

0.4 g of 2,4,6-triaminopyrimidine (F.W.125.14) was dissolved in 5 ml of deionized (DI) water and added, with stirring, to a solution of 40 g of an acid of formula

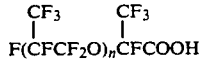

having an average molecular weight of 4000 in a FREON 113 solvent (50 ml). (FREON is a trademark of E. I. DuPont de Nemours & Co., Wilmington, Del. for chlorofluorocarbons.) The solution turned milky immediately and appeared to thicken. After 2 hours of continuous stirring the two phases were separated and the solvent of the organic phase was removed by evaporation. 39 g of amber colored oily material were recovered. Infrared spectral bands, including a series of bands centered about 3450, 3350 and 3180 cm$^{-1}$ ($\nu$N-H in varying degrees of association), 1690 cm$^{-1}$ ($\nu$C=O of CO$_2$—NH$_3$ and a red shift of about 190 cm$^{-1}$ from that of the fluorinated acid) and 1300, 1240, 1180 cm$^{-1}$ ($\nu$CF$_2$rCF$_2$); also bands near 1610, 980 and 780 cm$^{-1}$ (attributable to the heterocyclic ring) of the oily material were observed.

These spectral characteristics are consistent with the following structure:

wherein C$_4$N$_2$ is:

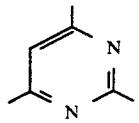

EXAMPLE 2

Thiourea salts of perfluoropolyether acid moieties, containing two long chain perfluoropolyether moieties on a polar thiourea base, are prepared as follows:

0.4 g of thiourea are dissolved in 10 ml of deionized water. 40 g of an acid of the formula:

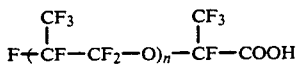

is dissolved in 50 ml of FREON 113, added to the thiourea solution with stirring, and heated for 2 hours. The two phases are separated; the lower organic phase is washed with deionized water, then the solvent is evaporated. A light colored liquid is obtained. The IR spectrum includes absorption bands near 3600 CM-1 ($\nu$N-H, broad), 1820 cm-1 ($\nu$C=S), 1670 cm-1 ($\nu$C=O of —CO$_2$NH$_3$), 1280, 1240, and 1180 cm-1 due to —CF$_2$, also 1030, 860 and 800 cm-1, among others, due to the perfluoropolyether acid. These spectral characteristics are consistent with the following structure:

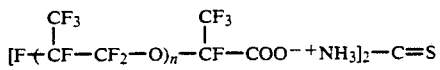

Other exemplary amines are melamine and tetrakis(3-aminopropyl) tetramethyl cyclotetrasiloxane. Other exemplary fluorocarbons are perfluorododecyl iodide and fluoroalkylsulfonic and fluoroalkylphosphoric acids such as DuPont's Zonyl TBS and UR materials.

EXAMPLE 3

The condensation product of phosphonitrilic chloride and a trifluoroalkylcitrate was prepared. The product contained 18 fluorocarbon chains on a phosphorus and nitrogen aromatic heterocyclic ring.

1.1 g of phosphonitrilic chloride trimer (P$_3$N$_3$Cl$_6$) having the following nuclear formula:

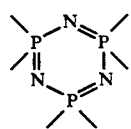

was dissolved in chloroform (25 ml), then was added dropwise to 11.4 g of a trifluoroalkyl citrate having this structure:

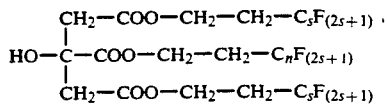

(mw ~1600, n is 6, 8, 10, 12, or 14, mostly 8 or 10), in FREON 112 (50 ml) and triethylamine (10 ml) while stirring and heating. Refluxed overnight, 10 g of light amber material were recovered. Major IR bands were observed near 2960 cm-1 ($\nu$CH$_2$), 1750 cm-1 ($\nu$CH$_2$), 1750 cm-1 ($\nu$C=O, —CO$_2$), 1200 cm-1 (CF$_2$, CF$_3$ broad), and 1040 cm-1 (possibly P—O—C). This spectrum is consistent with six terminal groups having the following structure:

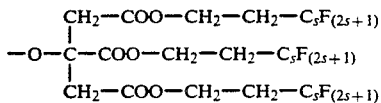

on the following nucleus:

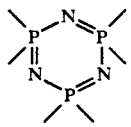

The IR absorption bands due to phosphonitrilic chloride near 1240 cm-1 (main) and 1300, 1190, 1140 and 980 cm-1 (minor) were masked by the absorption bands of the CF$_2$ and CF$_3$ fluoroalkyls.

EXAMPLE 4

Perfluoropolyether amines of triaminopyrimidine and 3 long chain perfluoropolyethers were formed as follows: 20 g of a diol of the formula:

$$HOCH_2CF_2O(CF_2O)_a(CF_2CF_2O)_bCF_2CH_2OH$$

having a molecular weight of about 4000, FREON 122 (25 ml), and 5 ml of triethylamine were mixed Then a xylene solution of tosyl chloride (1.9 g in 25 ml) was added and the mixture was stirred for 2 hours. Then an aqueous of triaminopyrimidine, (NH$_2$)$_3$C$_4$N$_2$, containing 0.4 g of LiOH (0.4 g/10 ml) was added. After refluxing overnight 20 g of a light viscous liquid were obtained. Its significant IR bands included 3500 cm$^{-1}$ (—NH—), 2950 cm$^{-1}$ (CH$_2$), 1600 cm$^{-1}$ (heterocyclic), 1200-1100 cm$^{-1}$ (CF$_2$). These bands are consistent with the following structure:

$$[HOCH_2CF_2O(CF_2O)_a(CF_2CF_2O)_bCF_2CH_2NH]_3T$$

wherein T has the following structure:

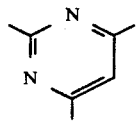

I claim:
1. A lubricated magnetic medium comprising a polar magnetic medium surface covered with a monolayer, wherein said monolayer has the nuclear structure:

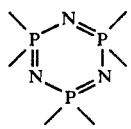

substituted at each free position with the substituent:

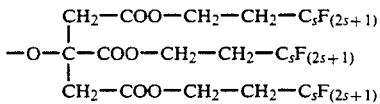

wherein s is between about 6 and about 14.

2. The lubricated magnetic medium of claim 1, wherein said lubricant is a Langmuir-Blodgett monolayer.

* * * * *